(12) United States Patent
Matsuzawa et al.

(10) Patent No.: US 9,670,532 B2
(45) Date of Patent: Jun. 6, 2017

(54) CHEMICAL SENSOR, CHEMICAL SENSOR MODULE, BIOMOLECULE DETECTION APPARATUS, AND BIOMOLECULE DETECTION METHOD

(71) Applicant: Sony Corporation, Tokyo (JP)

(72) Inventors: Nobuyuki Matsuzawa, Tokyo (JP); Kensaku Maeda, Kanagawa (JP); Yusuke Moriya, Kanagawa (JP); Ken Ozawa, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 91 days.

(21) Appl. No.: 14/348,988

(22) PCT Filed: Oct. 11, 2012

(86) PCT No.: PCT/JP2012/006509
§ 371 (c)(1),
(2) Date: Apr. 1, 2014

(87) PCT Pub. No.: WO2013/057905
PCT Pub. Date: Apr. 25, 2013

(65) Prior Publication Data
US 2014/0295577 A1    Oct. 2, 2014

(30) Foreign Application Priority Data

Oct. 21, 2011 (JP) ................................. 2011-231470

(51) Int. Cl.
*C12Q 1/68* (2006.01)
*G01N 21/64* (2006.01)
(Continued)

(52) U.S. Cl.
CPC ....... *C12Q 1/6834* (2013.01); *G01N 21/6454* (2013.01); *G01N 33/54373* (2013.01); *G01N 33/582* (2013.01)

(58) Field of Classification Search
None
See application file for complete search history.

(56) References Cited

U.S. PATENT DOCUMENTS 6,221,687 B1 * 4/2001 Abramovich ..... H01L 27/14601
438/69
7,078,172 B1 * 7/2006 Okamura ............. C12Q 1/6837
435/6.1
(Continued)

FOREIGN PATENT DOCUMENTS

CN        1606693 A     4/2005
CN      101001692 A     7/2007
(Continued)

OTHER PUBLICATIONS

Japanese Patent Office Action corresponding to Japanese Serial No. 2012-80050546.7 dated Sep. 30, 2015.
(Continued)

*Primary Examiner* — Robert T Crow
(74) *Attorney, Agent, or Firm* — Dentons US LLP (57) ABSTRACT

A chemical sensor including a substrate, an on-chip lens layer, and a flattening layer. On the substrate, a plurality of photodiodes are formed and arranged in a planar form. The on-chip lens layer collects incident light to the photodiodes and is provided on the substrate. The flattening layer covers and planarizes the on-chip lens to form a probe holding surface for holding a probe material.

19 Claims, 5 Drawing Sheets

(51) Int. Cl.
*G01N 33/543* (2006.01)
*G01N 33/58* (2006.01)

(56) References Cited

U.S. PATENT DOCUMENTS

| | | | | |
|---|---|---|---|---|
| 2003/0035755 | A1* | 2/2003 | Chen | G01N 21/645 422/52 |
| 2003/0077380 | A1* | 4/2003 | Lefkowitz | B01J 19/0046 427/2.1 |
| 2004/0211884 | A1* | 10/2004 | Fang | H01L 27/14601 250/214.1 |
| 2006/0254910 | A1 | 11/2006 | Kawarada | |
| 2007/0040194 | A1* | 2/2007 | Misawa | H01L 27/14623 257/291 |
| 2007/0080415 | A1* | 4/2007 | Cho | H01L 27/14627 257/432 |
| 2010/0204064 | A1* | 8/2010 | Cho | G01N 21/6454 506/17 |

FOREIGN PATENT DOCUMENTS

| | | |
|---|---|---|
| JP | 2001-358320 A | 12/2001 |
| JP | 2006-004991 | 1/2006 |

OTHER PUBLICATIONS

Supplementary European Search Report issued in connection with related EP Patent Application No. EP 12842402 dated Feb. 10, 2015.
Chinese Office Action corresponding to Chinese Serial No. 201280050546.7 dated May 13, 2016.

* cited by examiner

| Chemical sensor | Surface material quality | Distance | Lens | Sequence | Fluorescence intensity (relative value) | Ratio |
|---|---|---|---|---|---|---|
| Chemical sensor A | Diamond | 7 μm | With | Sequence 1 | 210 | 105 |
| | | | | Sequence 2 | 2 | |
| Chemical sensor B | Si oxide film | 7 μm | With | Sequence 1 | 205 | 21 |
| | | | | Sequence 2 | 10 | |
| Chemical sensor C | Diamond | 11 μm | With | Sequence 1 | 120 | 60 |
| | | | | Sequence 2 | 2 | |
| Chemical sensor D | Si oxide film | 11 μm | With | Sequence 1 | 124 | 21 |
| | | | | Sequence 2 | 6 | |
| Chemical sensor E | Diamond | 7 μm | Without | Sequence 1 | 101 | 101 |
| | | | | Sequence 2 | 1 | |
| Chemical sensor F | Si oxide film | 7 μm | Without | Sequence 1 | 105 | 15 |
| | | | | Sequence 2 | 7 | |
| Chemical sensor G | Diamond | 10 μm | With | Sequence 1 | 200 | 100 |
| | | | | Sequence 2 | 2 | |
| Chemical sensor H | Si oxide film | 10 μm | With | Sequence 1 | 190 | 21 |
| | | | | Sequence 2 | 9 | |

FIG.5

SEQUENCE LISTING

<160> NUMBER OF SEQ ID NOS: 3

<210> SEQ ID NO 1
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 1
aaaataaaat aaaataaaat                                           20

<210> SEQ ID NO 2
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 2
ttttatttta ttttatttta                                           20

```
<210> SEQ ID NO 3
<211> LENGTH: 20
<212> TYPE: DNA
<213> ORGANISM: Artificial Sequence
<220> FEATURE:
<223> OTHER INFORMATION: Synthetic nucleotide

<400> SEQUENCE: 3
ccccgccccg ccccgccccg                                              20
```

CHEMICAL SENSOR, CHEMICAL SENSOR MODULE, BIOMOLECULE DETECTION APPARATUS, AND BIOMOLECULE DETECTION METHOD

TECHNICAL FIELD

The present technology relates to a chemical sensor for detecting a biomolecule on the basis of fluorescence emission, a chemical sensor module on which the chemical sensor is mounted, a biomolecule detection apparatus, and a biomolecule detection method that uses the biomolecule detection apparatus.

BACKGROUND ART

In recent years, in the fields of medicine, biochemistry, molecular biology, and the like, it has become important to detect biomolecules such as proteins, various antigen molecules, DNA (deoxyribonucleic acid), and RNA (ribo nucleic acid). In particular, the amount of samples of those biomolecules is very small, from pmol to fmol order, depending on cases, so a development of a highly sensitive and highly accurate detection method is demanded.

As a highly sensitive detection method, a method of detecting fluorescence is most typically used. In the detection method of the fluorescence, for example, a target material to be detected is labeled in advance with a fluorescent marker, and an optical sensor to which a probe material that mutually acts with the target material specifically is fixed is used to detect the fluorescence from the target material that is adsorbed to the probe material.

For example, Patent Document 1 discloses an organic molecule detection semiconductor element in which a silicon substrate on which an organic molecule probe disposition area is formed and a solid state image pickup element are integrated with each other. The element has the structure in which fluorescence generated by bonding a target material with an organic molecule probe disposed in the organic molecule probe disposition area is detected by the solid state image pickup element.

Further, Patent Document 2 discloses a biopolymer analysis chip in which an on-chip lens is provided between spots formed of a double gate transistor (photoelectric conversion element) and a probe material. On the chip, fluorescence generated from the target material that is bonded with the probe material is collected by the on-chip lens and is detected by the double gate transistor.

Patent Document 1: Japanese Patent Application Laid-open No. 2002-202303
Patent Document 2: Japanese Patent Application Laid-open No. 2006-4991

SUMMARY OF INVENTION

Problem to be Solved by the Invention

In the structure disclosed in Patent Document 1, however, an optical system is not provided which guides isotropic light emitted from the organic molecule probe to the solid state image pickup element, so it is impossible to obtain a sufficient light quantity. Therefore, the sensitivity is low, and the accuracy is degraded. Further, the isotropic light may enter an adjacent solid state image pickup element, and a crosstalk may be generated in a detection signal. Furthermore, a material of a surface to which the organic molecule probe is bonded is not defined, and an improvement of detection accuracy by uniformly bonding the organic molecule probe on the surface is not achieved.

In addition, in the structure disclosed in Patent Document 2, on an upper surface of the on-chip lens, a light transmission top gate electrode is formed. Such a top gate electrode is thought to be formed of an ITO (Indium Tin Oxide), graphene, or the like as a light transmission electrode material. However, to obtain a low resistance, those materials have to have a large film thickness. This may degrade a light transmittance of the film and cause sensitivity degradation.

In view of the above-mentioned circumstances, an object of the present technology is to provide a chemical sensor capable of detecting a biomolecule with high accuracy, a chemical sensor module, a biomolecule detection apparatus, and a biomolecule detection method.

Means for Solving the Problem

To achieve the above-mentioned object, a chemical sensor according to an embodiment of the present technology includes a substrate, an on-chip lens, and a flattening layer.

On the substrate, a plurality of photodiodes are formed to be arranged in a planar form.

The on-chip lens collects incident light to the photodiodes, and is provided on the substrate.

The flattening layer covers and flattens the on-chip lens to form a probe holding surface for holding a probe material.

With this structure, light generated by bonding of the probe material held on the probe holding surface with a target material contained in a measurement target object is collected by the on-chip lens and enters the photodiodes, so it is possible to improve a light incident efficiency to the photodiodes and prevent leakage (crosstalk) of light to an adjacent photodiode.

The incident light may be fluorescence caused by bonding of the probe material with a target material.

With this structure, by detecting the fluorescence by the photodiodes the target material can be detected.

The chemical sensor may further include a spectral layer made of a spectral material laminated between the substrate and the on-chip lens or between the on-chip lens and the probe holding surface.

With this structure, even if light having a wavelength out of a detection target, for example, excitation light that causes fluorescence enters the chemical sensor, the light is attenuated by the spectral layer, so only light to be detected is detected by the photodiodes, that is, it is possible to detect light as the detection target with high accuracy.

The chemical sensor may further include a surface layer laminated on the flattening layer, the probe material being fixed to the surface layer.

With this structure, because the on-chip lens is flattened by the flattening layer, the surface layer can be formed, and the probe material can be fixed to the surface layer.

The surface layer may be made of diamond and subjected to a surface treatment by an irradiation with an ultraviolet ray in an ammonia gas atmosphere.

By irradiating the surface layer made of diamond with the UV ray in the ammonia gas atmosphere, the diamond can be aminated. As a result, by introducing carboxylic acid into the probe material, it is possible to generate amino bonding between the probe material and the diamond and thus chemically fix the probe material to the surface layer.

The surface treatment may be performed for areas of the on-chip lens, which are opposed to each other.

With this structure, the probe material is fixed to the area which has been subjected to the surface treatment, so the probe material is fixed to the surface layer with the material opposed to each on-chip lens. That is, light generated from the probe material on the areas is collected by the corresponding on-chip lenses, with the result that the light incident efficiency to the photodiodes is improved, and the crosstalk can be prevented.

The on-chip lens may be provided to each of the photodiodes on a one-to-one basis and collect incident light to each of the photodiodes.

With this structure, one on-chip lens collects light to one photodiode, so the light incident efficiency to the photodiodes is improved, and the crosstalk can be prevented as compared to the case where one on-chip lens collects light to a plurality of photodiodes.

The chemical sensor may further include a light shielding wall provided between the on-chip lenses.

With this structure, it is possible to completely prevent the crosstalk between the photodiodes adjacent to each other by the light shielding wall.

The flattening layer may be made of a material having a refractive index difference with the on-chip lens of 0.4 or more.

With this structure, a focal length of the on-chip lens can be set to be a focal length similar to the case where the flattening layer is replaced by air, that is, light can be effectively collected by the on-chip lens.

The chemical sensor may further include a probe material layer made of a probe material laminated on the flattening layer.

With this structure, light generated on the probe material layer can be detected with high accuracy as described above.

A distance between the probe material layer and the photodiodes may be 10 µm or less.

With this structure, it is possible to sufficiently collect light generated on the probe material layer to the photodiodes.

The probe material layer may be sectioned to face the on-chip lenses, respectively.

With this structure, different probe materials are used for the probe material layers sectioned, thereby making it possible to detect various target materials at the same time.

The probe material may be one of DNA, RNA, a protein, and an antigen.

The chemical sensor according to the present technology, it is possible to use those biomolecules as the probe material.

To achieve the above object, a chemical sensor module according to an embodiment of the present technology includes a chemical sensor and an excitation light source.

The chemical sensor includes a substrate on which a plurality of photodiodes are formed to be arranged in a planar form, an on-chip lens to collect incident light to the photodiodes, which is provided on the substrate, and a flattening layer to cover and flatten the on-chip lens to form a probe holding surface for holding a probe material.

The excitation light source irradiates the chemical sensor with excitation light, and the excitation light source is provided integrally to the chemical sensor.

To achieve the above object, a biomolecule detection apparatus according to an embodiment of the present technology includes a chemical sensor and a signal processing circuit.

The chemical sensor includes a substrate on which a plurality of photodiodes are formed to be arranged in a planar form, an on-chip lens to collect incident light to the photodiodes, which is provided on the substrate, and a flattening layer to cover and flatten the on-chip lens to form a probe holding surface for holding a probe material.

The signal processing circuit processes an output signal of the photodiodes, which is connected to the chemical sensor.

To achieve the above object, a biomolecule detection method according to an embodiment of the present technology includes preparing a chemical sensor including a substrate on which a plurality of photodiodes are formed to be arranged in a planar form, an on-chip lens to collect incident light to the photodiodes, which is provided on the substrate, and a flattening layer to cover and flatten the on-chip lens to form a probe holding surface for holding a probe material.

A probe material layer is formed by laminating a probe material on the flattening layer.

A measurement target substance is brought into contact with the probe material layer to bond a target material contained in the measurement target substance with the probe material.

A measurement target substance which is not bonded with the probe material is removed.

The chemical sensor is irradiated with excitation light.

Fluorescence caused by the bonding of the target material with the probe material is detected by the photodiodes.

In the step of detecting the fluorescence, changes in wavelength and brightness of fluorescence by a mutual action of the target material and the probe material fluorescently labeled in advance may be detected by the photodiodes.

In the step of detecting the fluorescence, fluorescence by a target material fluorescently labeled in advance and bonded with the probe material may be detected by the photodiodes.

In the step of detecting the fluorescence, a bonded body of the probe material and the target material may be fluorescently labeled, and fluorescence thereof may be detected by the photodiodes.

Effect of the Invention

As described above, according to the present technology, it is possible to provide the chemical sensor capable of detecting a biomolecule with high accuracy, the chemical sensor module, the biomolecule detection apparatus, and the biomolecule detection method.

MODE(S) FOR CARRYING OUT THE INVENTION

First Embodiment

A biomolecule detection apparatus according to a first embodiment of the present technology will be described.

(Entire Structure of Biomolecule Detection Apparatus)

Figure 1:
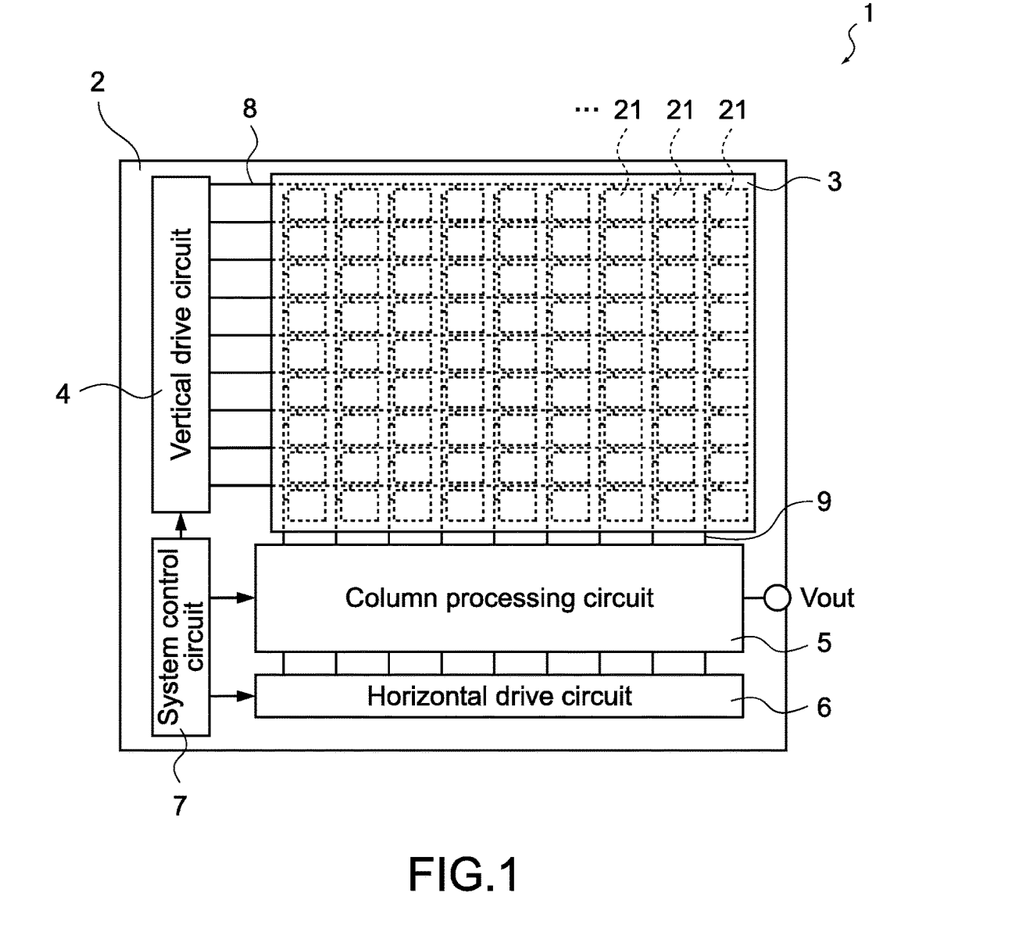
FIG. 1 A schematic diagram showing the structure of a biomolecule detection apparatus according to a first embodiment of the present technology.

FIG. 1 is a schematic diagram showing the structure of a biomolecule detection apparatus 1 according to this embodiment. As shown in the figure, the biomolecule detection apparatus 1 is constituted of a chemical sensor 3 provided on a substrate 2 and a peripheral circuit for driving the chemical sensor 3. The chemical sensor 3 has a plurality of photodiodes 21 arranged on the substrate 2 as will be described later.

The number of photodiodes 21 and the arrangement thereof are not limited and can be changed as appropriate. Here, the photodiodes 21 are arranged in a matrix pattern on a plane of the substrate 2. A row direction is set as a vertical direction, and a column direction is set as a horizontal direction.

The peripheral circuit is constituted of a vertical drive circuit 4, a column signal processing circuit 5, a horizontal drive circuit 6, and a system control circuit 7. Further, the photodiodes 21 are connected to pixel drive lines 8 for each row and connected to vertical signal lines 9 for each column. The pixel drive lines 8 are connected to the vertical drive circuit 4, and the vertical signal lines 9 are connected to the column signal processing circuit 5.

The column signal processing circuit 5 is connected to the horizontal drive circuit 6, and the system control circuit 7 is connected to the vertical drive circuit 4, the column signal processing circuit 5, and the horizontal drive circuit 6. It should be noted that the peripheral circuit can be disposed on a position of being laminated on a pixel area or a position opposite to the substrate 2, for example.

The vertical drive circuit 4 is formed of a shift register, for example. The vertical drive circuit 4 selects the pixel drive line 8, supplies a pulse for driving the photodiodes 21 to the pixel drive line 8 selected, and drives the photodiodes 21 on a row basis. In other words, the vertical drive circuit 4 performs selective scanning for the photodiodes 21 in the vertical direction sequentially on the row basis. Then, through the vertical signal line 9 vertically wired with respect to the pixel drive line 8, the vertical drive circuit 4 supplies, to the column signal processing circuit 5, a pixel signal based on a signal charge generated in accordance with a received light quantity in the photodiodes 21.

The column signal processing circuit 5 performs a signal processing such as a noise removal for each pixel column with respect to a signal output from the photodiodes 21 of one row. In other words, the column signal processing circuit 5 performs signal processing such as a correlated double sampling (CDS), a signal amplification, and an analog/digital (AD) conversion for removing a fixed pattern noise specific to a pixel.

The horizontal drive circuit 6 is formed of the shift register, for example, and sequentially outputs horizontal scanning pulses, thereby selecting the column signal processing circuits 5 in order and causing each column signal processing circuit 5 to output a pixel signal.

The system control circuit 7 receives an input clock and data that specifies an operation mode or the like and outputs data relating to inside information or the like of the chemical sensor 3. That is, on the basis of a vertical synchronizing signal, a horizontal synchronizing signal, and a master clock, the system control circuit 7 generates a clock signal and a control signal which are references of the operations of the vertical drive circuit 4, the column signal processing circuit 5, the horizontal drive circuit 6, and the like. Then the system control circuit 7 inputs those signals to the vertical drive circuit 4, the column signal processing circuit 5, the horizontal drive circuit 6, and the like.

As described above, the vertical drive circuit 4, the column signal processing circuit 5, the horizontal drive circuit 6, the system control circuit 7, and a pixel circuit (to be described later) provided to the photodiodes 21 constitute a drive circuit that drives the photodiodes 21.

(Structure of Chemical Sensor)

The structure of the chemical sensor 3 will be described.

Figure 2:
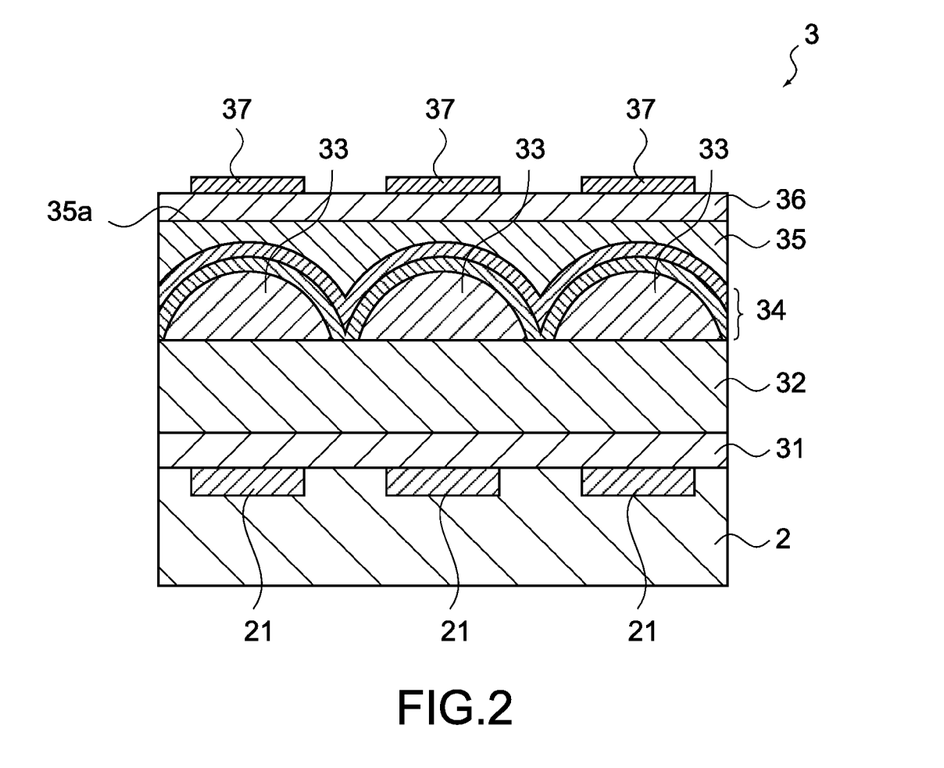
FIG. 2 A cross-sectional view showing the structure of a chemical sensor according to the first embodiment of the present technology.

FIG. 2 is a cross-sectional view showing the structure of the chemical sensor 3 according to this embodiment. As shown in the figure, the chemical sensor 3 includes the photodiodes 21 formed on the substrate 2, a protection insulating layer 31 formed on the substrate 2, a spectral layer 32, on-chip lenses 33, an antireflection layer 34, a flattening layer 35, a surface layer 36, and probe material layers 37.

On the substrate 2, the protection insulating layer 31 is laminated, and on the protection insulating layer 31, the spectral layer 32 is laminated. On the spectral layer 32, the on-chip lenses 33 are formed, and the on-chip lenses 33 are covered with the antireflection layer 34. On the antireflection layer 34, the flattening layer 35 is laminated, and on the flattening layer 35, the surface layer 36 is laminated. On the surface layer 36, the probe materials 37 are laminated.

The substrate 2 is made of single crystal silicon, for example, and has a light receiving surface on one principal surface side of the substrate 2. On the surface layer on the light receiving surface side, the photodiodes 21 each formed of an impurity region are formed. The photodiodes 21 are arranged two-dimensionally as shown in FIG. 1.

It should be noted that the photodiodes 21 may be provided only on the one principal surface side as the light receiving surface side of the substrate 2 as shown in the figure or may be provided over the one principal surface side and another principal surface side. The chemical sensor 3 can have an element structure of a CMOS (Complementary Metal Oxide Semiconductor) or a CCD (Charge Coupled Device) type. When necessary, another impurity region such as a floating diffusion or an element isolation (not shown) is formed therein.

Further, on the substrate 2 provided with the impurity region including the photodiode 21, a gate insulating film (not shown), a gate electrode (not shown), or the like may be disposed. In this case, the protection insulating layer 31 is disposed so as to cover the gate insulating film or the gate electrode. Further, a pixel circuit including the gate insulating film or the gate electrode may be disposed on a side opposite to the light receiving surface of the substrate 2.

The protection insulating layer 31 is made of an insulating material and insulates the substrate 2 from an upper layer. It is necessary for the protection insulating layer 31 to cause at least a fluorescent wavelength to pass therethrough.

The spectral layer 32 attenuates an excitation light wavelength and is made of a spectral material that causes a fluorescent wavelength to pass therethrough. The spectral layer 32 may be a color filter that uses a pigment or a dye or may be a color filter that uses a multilayer film interference. It should be noted that the spectral layer 32 may be disposed on a different position, for example, between the flattening layer 35 and the surface layer 36.

The on-chip lenses 33 collect the incident fluorescence to the photodiodes 21. The on-chip lenses 33 are provided so as to correspond to the photodiodes 21, and can have a hemispherical shape which is convex with respect to a light incident direction. It should be noted that one on-chip lens 33 may be provided to the plurality of photodiodes 21, but providing one on-chip lens 33 to one photodiode 21 enables efficient light collection.

Further, the shape of the on-chip lens 33 is not limited to the hemispherical shape and can have another lens shape. In the following, the refractive index of the on-chip lens 33 is set to n0. It should be noted that the refractive index n0 and a refractive index indicated in the following are set to be a reflective index with respect to a wavelength λ of 550 nm in the vicinity of the center of visible light, which is an image pickup wavelength.

The on-chip lens 33 is made of a material having a transmission property in at least a fluorescence wavelength region of a detection target, and preferably made of a material having a larger difference in refractive index with the flattening layer 35 to be described later. Examples of the material include silicon nitride (refractive index n0=1.9), silicon nitride oxide (refractive index n0=1.85), titanium oxide dispersion polysiloxane resin (refractive index n0=1.8), titanium oxide dispersion acrylic resin (refractive index n0=1.8), and the like.

The antireflection layer 34 is a layer for preventing a reflection on the surface of the on-chip lenses 33, and is capable of being formed in a conformal manner along the on-chip lenses 33. The antireflection layer 34 can be formed of silicon nitride oxide or the like and can have a multilayer structure as shown in the figure.

The flattening layer 35 covers the on-chip lenses 33 and has a probe holding surface 35a in parallel to the substrate 2. The on-chip lenses 33 are each formed into a hemispherical lens shape, for example, and the flattening layer 35 buries the shape to form the probe holding surface 35a for holding the probe material. The flattening layer 35 is formed of a material having a refractive index which has a sufficiently large difference with the refractive index n0 of the on-chip lens 33 to such an extent that a light collection characteristic to the photodiodes 21 by the on-chip lenses 33 is maintained. In the following description, the refractive index of the flattening layer 35 is set as a refractive index n1.

Here, since the on-chip lens 33 has the convex lens shape, the flattening layer 35 is formed of a material having a small refractive index, and a relationship between the refractive index n0 of the on-chip lens 33 and the refractive index n1 of the flattening layer 35 satisfies n1<n0. The thickness of the flattening layer 35 only has to be set to such a thickness that the lens shape of the on-chip lenses 33 can be buried.

For the on-chip lens 33, a focal length is determined which is small to the same extent as the case where the flattening layer 35 is replaced with air, and a material that satisfies a refractive index difference |n0−n1|≥0.4 is selected therefor. In selecting the material that forms the flattening layer 35, it is unnecessary to consider thickening of the flattening layer 35.

Specifically, in the case where the on-chip lens 33 is formed of silicon nitride (refractive index n0=1.9), it is desirable that the flattening layer 35 is formed of a material having a refractive index n1 of 1.5 or less. Examples of such a material include fluorine-containing polysiloxane resin (refractive index n1=1.42), fluorine-containing acrylic resin (refractive index n1=1.42), hollow silica particles containing polysiloxane resin (refractive index n1=1.35), and the like.

The surface layer 36 is a layer to which the probe material is fixed. The surface layer 36 is capable of being formed to be flat because the on-chip lenses 33 are flattened by the flattening layer 35. The surface layer 36 can be formed of diamond, silicon nitride, silicon oxide, or the like. Out of those materials, when diamond is used, it is possible to form a strong bonding between the probe material and the surface layer 36 by the surface treatment to be described later.

The surface layer 36 is capable of being subject to a surface treatment for improving coherence with the probe material. In the case where the surface layer 36 is made of diamond, it is possible to carry out amination by irradiation with UV rays in an ammonia gas atmosphere. As a result, in fixing the probe material to the surface layer 36, a carboxylic acid is introduced into the probe material, thereby generating amino bonding between the surface layer 36 and the probe material, with the result that the both are chemically fixed to each other. Further, in the case where the surface layer 36 is made of silicon oxide, a functional group is introduced by a silane coupling treatment, thereby making it possible to perform bonding with the probe material.

It should be noted that the surface treatment can be carried out not on the entire surface layer 36 but on an arbitrary area thereof. By carrying out the surface treatment for each area opposed to the on-chip lens 33, it is possible to fix the probe material to be described later to the surface layer 36 for each on-chip lens 33.

The chemical sensor 3 can be offered to a user in this state, and the user can use the chemical sensor by fixing an arbitrary probe material to the probe holding surface 35a.

The probe material layers 37 are each formed of a probe material (DNA (deoxyribonucleic acid), an RNA (ribo nucleic acid), proteins, or antigen, and are fixed to the probe holding surface 35a. In the case where the surface treatment is carried out with respect to the areas opposed to the on-chip lenses 33 of the probe holding surface 35a as described above, the probe material layers 37 are formed only on the areas which have been subjected to the surface treatment. As a result, the areas of the probe material layers 37 correspond to the on-chip lenses 33 and the photodiodes 21 on a one-to-one basis, thereby making it possible to detect fluorescence with high accuracy.

It is desirable that a distance between the probe material layers 37 and the photodiodes 21 is set to be equal to or less than 10 μm. If the distance is more than 10 μm, light emitted from the probe material layers 37 is not sufficiently collected to the photodiodes 21, which may cause deteriorations of the sensitivity and the accuracy.

The chemical sensor 3 is formed as described above. The fluorescence generated from the probe material layers 37 is collected to the photodiodes 21 by the on-chip lenses 33 and detected. Since the probe material layers 37 are laminated on the flattening layer 35 or on the surface layer 36 formed directly thereabove, it is possible to set the distance from the probe material layers 37 to the photodiodes 21 to be short, thereby making it possible to improve the light collecting efficiency of the fluorescence.

(Method of Manufacturing Chemical Sensor)

A method of manufacturing the chemical sensor 3 will be described.

First, on one principal surface side of the substrate 2 made of single crystal silicon or the like, the photodiodes 21 each formed of an impurity region are formed by an ion injection and a heat treatment over a mask. Further, inside the substrate 2, another impurity region may be formed, and a gate insulating film and a gate electrode may be further formed on the substrate.

Subsequently, on the substrate 2 in which the photodiodes 21 are formed, the protection insulating layer 31 is laminated. At this time, in consideration of the focal length of the on-chip lenses 33 formed thereafter, it is desirable that the protection insulating layer 31 has such a thickness that a focal point of the on-chip lens 33 is positioned in the photodiode 21.

Further, on the protection insulating layer 31, the spectral layer 32 is laminated. The spectral layer 32 can be laminated by spin coating or the like. Then, on the spectral layer 32, the on-chip lenses 33 are formed. The on-chip lenses 33 can be formed by forming a film made of a structural material (hereinafter, referred to as material film) of the on-chip lens 33 and molding the film.

Specifically, on the material film, island-shaped resist patterns corresponding to the photodiodes 21 are formed. After that, the resist patterns are caused to flow by melt flowing and are each molded into the convex lens shape by surface tension.

Over the resist patterns each having the convex lens shape, the material film is etched along with the resist patterns, with the result that a curved surface shape of the resist pattern can be transferred onto the material film. As a result, the convex on-chip lenses 33 can be formed above the photodiodes 21, respectively. On the on-chip lenses 33, the antireflection layer 34 can be laminated as necessary.

Subsequently, on the on-chip lenses 33 (or on the antireflection layer 34), the flattening layer 35 is laminated. The flattening layer 35 can be laminated by spin coating or the like. Here, in the case where a solution of a structural material (hereinafter, referred to as material solution) of the flattening layer 35 has a low viscosity, there is a limitation on a solution coating thickness by the spin coating on the on-chip lenses 33.

However, it is only necessary to bury the lens shape of the on-chip lenses 33 and apply the material solution, so an increase of the coating film thickness is not necessary. For example, it is possible to apply the material solution with the coating film thickness of approximately 1 μm from a top portion of the on-chip lens 33. In fact, in the case where the material solution has the low viscosity, a burying performance of the on-chip lenses 33 becomes desirable, with the result that it is possible to provide a desirable image quality with less image quality defects due to a void. After that, by a heat treatment or the like, the material solution is cured, with the result that the flattening layer 35 can be formed.

Further, when necessary, the surface layer 36 is laminated on the flattening layer 35. The surface layer 36 can be formed by a CVD (Chemical Vapor Deposition) or the like. The surface layer 36 can be subjected to the surface treatment for improving the bonding property with the probe material as described above. It should be noted that the surface treatment can be carried out only on areas opposed to the on-chip lenses 33.

Finally, on the surface layer 36 or on the flattening layer 35, the probe material layer 37 is laminated. The probe material layer 37 can be formed by performing dripping or the like of the probe material onto the surface layer 36 or the flattening layer 35 to be bonded. In the case where the surface layer 36 is subjected to the surface treatment, it is possible to laminate the probe material layer 37 only on the area which is subjected to the surface treatment.

The chemical sensor 3 can be manufactured as described above.

(Biomolecule Detection Method with Use of Chemical Sensor)

A description will be given on a biomolecule detection method with the use of the chemical sensor 3 described above.

In the detection of a target material, in the case where DNA is used as the probe material, it is possible to use 5'-fluorescein labeled DNA. With respect to the 5'-fluorescein labeled DNA, when DNA having a complementary sequence is contained in a sample, a hybridization reaction occurs, and the probe material is changed from single-stranded DNA (ss-DNA) to double-stranded DNA (ds-DNA). With this change, a dielectric constant around a fluorescent molecule is changed, thereby causing the fluorescent wavelength and intensity of the fluorescence to change. The photodiodes 21 detect the change.

Alternatively, in the case where DNA is used as the probe material, DNA which is not fluorescently labeled is used as the probe material, and the 5'-fluorescein labeled DNA is used for a sample, for example. In this case, when DNA having a complementary sequence with respect to the DNA as the probe material is contained in the sample, the hybridization reaction occurs, and the material becomes ds-DNA fluorescently labeled. The emission of the fluorescence from the fluorescent label is detected by the photodiodes 21.

Alternatively, in the case where DNA is used as the probe material, DNA which is not fluorescently labeled is used as the probe material, and a fluorescent dye is not also introduced into a sample.

In this case, when DNA having a complementary sequence with respect to the DNA as the probe material is contained in the sample, the hybridization reaction occurs, and the material becomes ds-DNA. Then, only the ds-DNA is selectively dyed to be fluorescently labeled by using a PicoGreen double-stranded DNA quantitative reagent (manufactured by Molecular Probes), for example, thereby introducing the fluorescent label into the ds-DNA part. The emission of the fluorescence from the fluorescent label is detected by the photodiodes 21.

The fluorescence caused by the bonding of the target material with the probe material, which is generated on the probe material layers 37 as described above, passes through the surface layer 36 and the flattening layer 35 and enters the on-chip lenses 33. At this time, the antireflection layer 34 formed on the surface of the on-chip lenses 33 prevents the reflection of the fluorescence. The fluorescence that enters the on-chip lenses 33 is collected by the on-chip lenses 33, excitation light is removed by the spectral layer 32, and light thus obtained passes through the protection insulating layer 31 and then reaches the photodiodes 21.

By collecting the fluorescence by the on-chip lenses 33, the intensity of the fluorescence that reaches the photodiodes 21 can be increased, and a crosstalk between adjacent photodiodes 21 can be prevented.

(Chemical Sensor Module)

Figure 3:
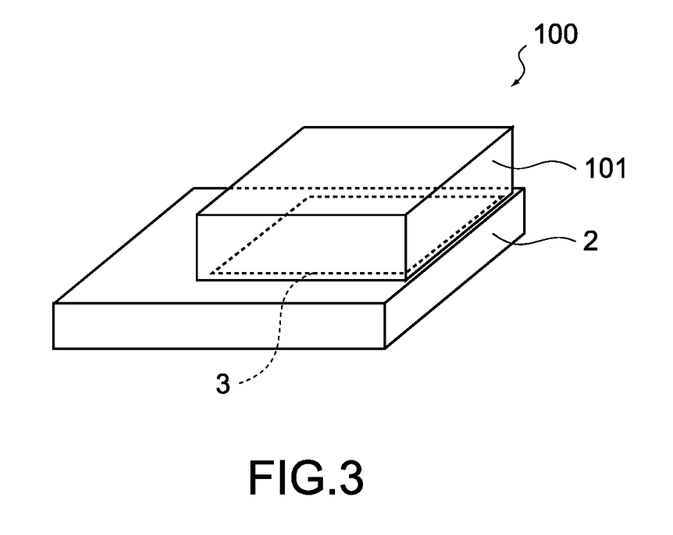
FIG. 3 A schematic diagram showing the structure of a chemical sensor module according to the first embodiment of the present technology.

The chemical sensor module 3 can form a module with an excitation light source that irradiates the chemical sensor 3 with excitation light. FIG. 3 is a schematic diagram showing a chemical sensor module 100. As shown in the figure, the chemical sensor module 100 is formed by connecting an excitation light source 101 to the chemical sensor 3 integrally. It should be noted that the excitation light source 101 is closely attached to the chemical sensor 3 in FIG. 3, but another form may be adopted. A distance may be given between the chemical sensor 3 and the excitation light source 101 to some extent.

Second Embodiment

A biomolecule detection apparatus according to a second embodiment of the present technology will be described. The biomolecule detection apparatus according to this embodiment is different from the biomolecule detection apparatus according to the first embodiment in the structure of the chemical sensor. In the following, in this embodiment, the description on the same structure as the biomolecule detection apparatus according to the first embodiment is omitted.

(Structure of Chemical Sensor)

Figure 4:
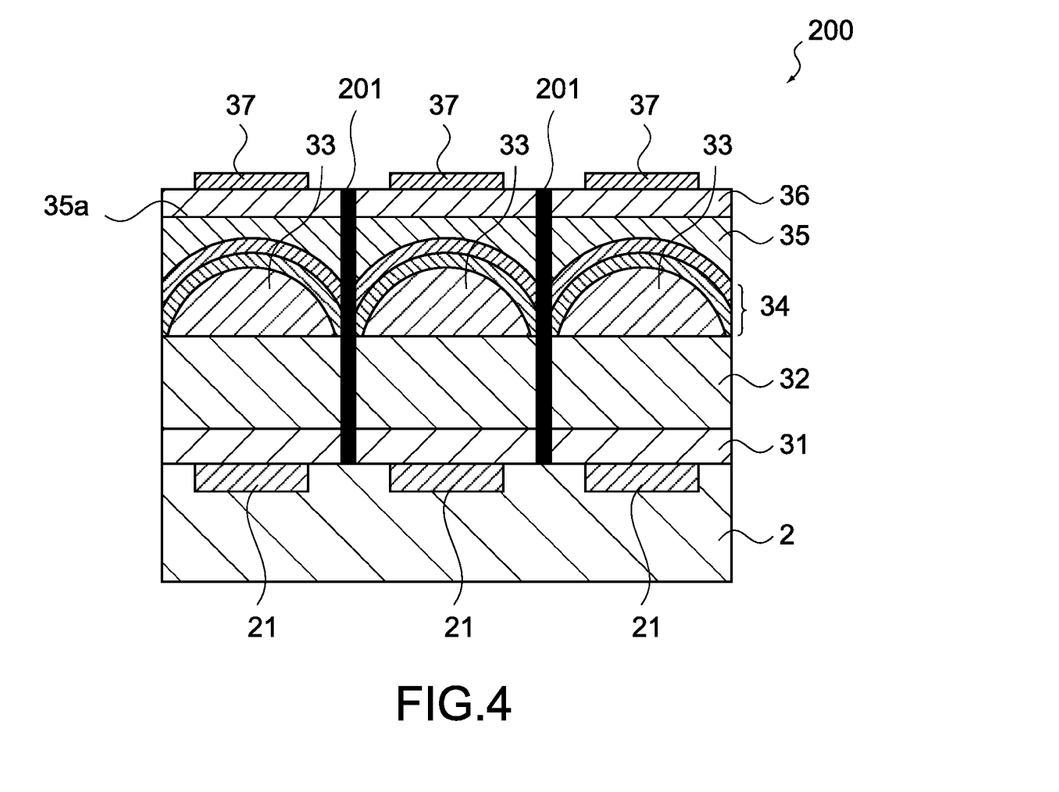
FIG. 4 A cross-sectional view showing the structure of a chemical sensor according to a second embodiment of the present technology.

The structure of a chemical sensor according to this embodiment will be described. FIG. 3 is a schematic diagram showing the structure of a chemical sensor 200 according to this embodiment. As shown in the figure, the chemical sensor 3 has light shielding walls 201 in addition to the structure of the chemical sensor 3 according to the first embodiment.

The light shielding wall 201 has the structure for preventing a crosstalk, that is, preventing the fluorescence generated from the probe material layer 37 corresponding to a specific photodiode 21 from being detected by an adjacent photodiode 21. The light shielding layers 201 can be formed between the on-chip lenses 33 while being extended from the flattening layer 35 to the protection insulating layer 31. Alternatively, the light shielding layers 201 may be extended for a part of the layer structure, specifically, for example, only for the flattening layer 35 or from the flattening layer 35 to the spectral layer 32.

The light shielding wall 201 can be formed as follows. That is, after the flattening layer 35 is formed, the photoresist is applied, and the patterning is performed, thereby removing the photoresist corresponding to a part where the light shielding wall 201 is formed. Then, the flattening layer 35 and the like are removed by the dry etching, and the photoresist is also removed, and subsequently a negative black resist is applied, to expose only a part where the light shielding wall 201 is formed to light. As a result, the light shielding wall 201 made of the black resist can be buried.

In the chemical sensor 200 according to this embodiment, the fluorescence generated from the probe material layer 37 corresponding to the specific photodiode 21 is shielded from light by the light shielding walls 201. With this structure, it is possible to prevent the crosstalk between the photodiodes 21, which can obtain high detection accuracy.

The present technology is not limited to the above embodiments and can be modified without departing from the gist of the present technology.

Examples

Chemical sensors shown in the following examples or comparative example were produced, and fluorescence intensities thereof were measured. The measurement results are shown in FIG. 4.

(Chemical Sensor A)

On one principal surface side of a substrate made of single crystal silicon, photodiodes each formed of an impurity region were formed by an ion injection over a mask and a heat treatment thereafter, another impurity region was formed inside the substrate, and a gate insulating film and a gate electrode were formed on the substrate. After that, a protection insulating layer was formed on the substrate. At this time, the protection insulating layer was set to have a thickness adjusted so that a focal point of an on-chip lens is positioned in the photodiode in consideration of a focal length of the on-chip lens formed later.

After that, on the protection insulating layer, a spectral layer formed of a red color filter (that causes light having a wavelength of 550 nm or more to pass therethrough) was formed. Then, on the spectral layer, the on-chip lenses made of silicon nitride (refractive index n0=1.9) were formed. At this time, a silicon nitride film was formed first on the spectral layer, and then an island-shaped resist pattern corresponding to each photodiode was formed.

Subsequently, the melt flowing was used to perform the heat treatment, thereby causing the resist pattern to flow and forming the shape thereof into a convex lens shape by surface tension. After that, above the resist pattern having the convex lens shape, the silicon nitride film was etched along with the resist pattern, and a curbed surface shape of the resist pattern was transferred onto the silicon nitride film. As a result, the convex on-chip lens made of silicon nitride was formed on each of the photodiodes.

Subsequently, a flattening layer was formed so as to bury the lens shape of the on-chip lens. In this case, a transparent material having a sufficient refractive index difference with respect to silicon nitride that forms the on-chip lens was used. As such a material, fluorine-containing polysiloxane resin (refractive index n1=1.42) was used in this case. The spin coating was used to form the flattening layer.

At this time, a solution obtained by dissolving the fluorine-containing polysiloxane resin into propylene glycol monomethyl ether acetate (PEGMEA) as a solvent was spin-coated on the on-chip lens. A saturation solubility of the fluorine-containing polysiloxane resin with respect to PEGMEA is small, and the solution has an extremely low viscosity, but the solution was applied with a thickness of approximately 1 μm from a top portion of the on-chip lens.

After that, a heat treatment of 120° C. for 1 minute was carried out to dry and remove the solvent in the solution applied on the on-chip lens. Subsequently, a heat treatment of 230° C. for 5 minutes was performed to sufficiently cure the fluorine-containing polysiloxane resin. As a result, the lens shape of the on-chip lens was buried, and thus the flattening layer made of the fluorine-containing polysiloxane resin molded to be flat was formed.

Next, a surface layer made of diamond was laminated by the CVD with the use of a mixed gas constituted of methane and hydrogen. Further, by the irradiation with UV rays in an ammonia gas atmosphere, the surface of diamond was aminated. A distance between photodiodes of the chemical sensor thus produced and the surface of the surface layer was 7 μm. The chemical sensor produced as described above is referred to as a chemical sensor A.

(Chemical Sensor B)

A surface layer was formed of an Si oxide instead of diamond in the chemical sensor A. Specifically, on a flattening layer, the Si oxide was laminated by the CVD. Further, the surface layer made of the Si oxide was subjected to oxygen asking, and a treatment was performed with an aminosilane coupling agent, to laminate the surface. The chemical sensor thus produced is referred to as a chemical sensor B.

(Chemical Sensor C)

In the chemical sensor A, when forming the flattening layer, a film thickness of spin coating was changed, and the coating of the flattening layer was repeated four times to thicken the flattening layer, thereby setting a distance between the photodiodes and the surface of the surface layer to 11 μm. The chemical sensor thus produced is referred to as a chemical sensor C.

(Chemical Sensor D)

In the chemical sensor B, when forming the flattening layer, a film thickness of spin coating was changed, and the coating of the flattening layer was repeated four times to thicken the flattening layer, thereby setting a distance between the photodiodes and the surface of the surface layer to 11 μm. The chemical sensor thus produced is referred to as a chemical sensor D.

(Chemical Sensor E)

In the chemical sensor A, the on-chip lenses were not formed, and transparent resin (acrylic type) was formed instead in the position of the on-chip lenses and the flattening layer so as to have the same thickness as the on-chip lenses and the flattening layer. The chemical sensor thus produced is referred to as a chemical sensor E.

(Chemical Sensor F)

In the chemical sensor B, the on-chip lenses were not formed, and transparent resin (acrylic type) was formed instead in the position of the on-chip lenses and the flattening layer so as to have the same thickness as the on-chip lenses and the flattening layer. The chemical sensor thus produced is referred to as a chemical sensor F.

(Chemical Sensor G)

In the chemical sensor A, when forming the flattening layer, the film thickness of spin coating was changed, the coating of the flattening layer was repeated four times to thicken the flattening layer, thereby setting the distance between the photodiodes and the surface of the surface layer to 10 μm. The chemical sensor thus produced is referred to as a chemical sensor G.

(Chemical Sensor H)

In the chemical sensor B, when forming the flattening layer, the film thickness of spin coating was changed, and the coating of the flattening layer was repeated four times to thicken the flattening layer, thereby setting the distance between the photodiodes and the surface of the surface layer to 10 μm. The chemical sensor thus produced is referred to as a chemical sensor H.

(Measurement of Fluorescence Intensity)

For each of the chemical sensors A to H produced as described above, the measurement of a fluorescence intensity was performed as follows.

Each of the chemical sensors was subjected to a treatment with a succinic acid to generate a carboxyl group on the surface, and then aminated oligonucleotide (DNA) was reacted to 5'-end. The oligonucleotide is 20 mer, and a sequence thereof is AAAATAAAATAAAATAAAAT (SEQ ID NO: 1) (buffer solution: PBS (Sodium phosphate: 10 mM; NaCl: 0.1 M)). The buffer solution was dripped to the chemical sensors to be left for 1 hour at 50° C.

For washing after the reaction, PBS-Tween (Sodium phosphate: 10 mM; NaCl: 0.1 M; 0.65% (w/v) Tween 20) was used.

In contrast, as sample DNAs, oligonucleotide having fluoresceinated 5'-end was prepared. It should be noted that sequences of the oligonucleotide prepared were TTTTATTT-TATTTTATTTTA (SEQ ID NO: 2), which is a complementary sequence with the above sequence (SEQ ID NO: 1), and CCCCGCCCCGCCCCGCCCCG (SEQ ID NO: 3), which is not a complementary sequence.

The PBS buffer solution of the sample DNAs was dripped on the chemical sensors, a hybridization reaction (1 hour) was caused to occur, and then the chemical sensors were washed with PBS-Tween.

The fluorescence intensity from each of the chemical sensors after the washing was measured by causing excitation with light having a wavelength of 490 nm. Due to the characteristic of the color filter of the sensor, the intensity of a component having a wavelength of 550 nm or more was measured out of the fluorescence from fluorescein. The intensities measured are shown in the table of FIG. 4. It should be noted that in the table, a "ratio" refers to an intensity ratio of the (SEQ ID NO: 2) to the (SEQ ID NO: 3). The larger the ratio is, the more an error detection can be reduced.

(About Measurement Result)

Figure 5:
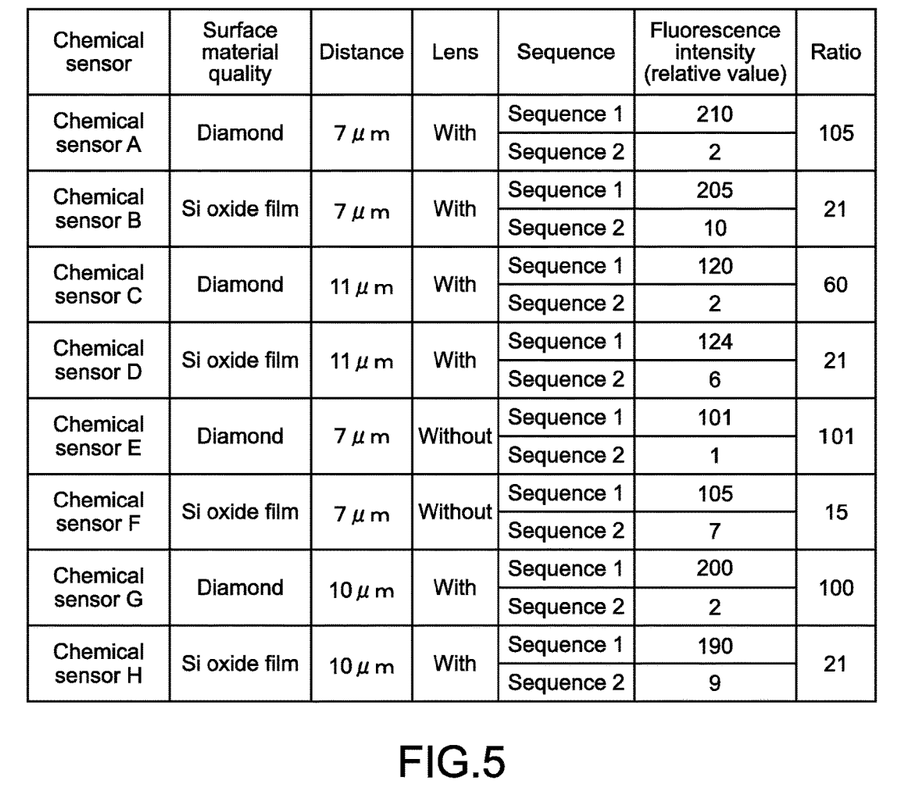
FIG. 5 A table showing results of examples.

To detect the sample DNA with a sufficient reliability, as the intensity, a brightness of approximately 200 or more is necessary in the measurement system used in this case. As is apparent from FIG. 5, if the distance between the photodiodes of the chemical sensor and the surface of the surface layer exceeds 10 μm, it is impossible to obtain a sufficient intensity. Further, the same holds true for the case where the on-chip lenses are eliminated, and it is also impossible to obtain the sufficient intensity. Furthermore, in terms of the intensity ratio of the SEQ ID NO: 2 to the SEQ ID NO: 3, a larger value is obtained in the case where the surface layer is formed of diamond as compared to the case where the surface layer is formed of the Si oxide film. That is, by using diamond as the material of the surface layer, it is possible to carry out the detection with desirable accuracy with less error detection.

It should be noted that the present technology can take the following configurations.

(1) A chemical sensor, including:
a substrate on which a plurality of photodiodes are formed to be arranged in a planar form;
an on-chip lens to collect incident light to the photodiodes, which is provided on the substrate; and
a flattening layer to cover and flatten the on-chip lens to form a probe holding surface for holding a probe material.

(2) The chemical sensor according to Item (1),
in which the incident light is fluorescence caused by bonding of the probe material with a target material.

(3) The chemical sensor according to Item (1) or (2), further including
a spectral layer made of a spectral material laminated between the substrate and the on-chip lens or between the on-chip lens and the probe holding surface.

(4) The chemical sensor according to any one of Items (1) to (3), further including
a surface layer laminated on the flattening layer, the probe material being fixed to the surface layer.

(5) The chemical sensor according to any one of Items (1) to (4),
in which the surface layer is made of diamond and is subjected to a surface treatment by an irradiation with an ultraviolet ray in an ammonia gas atmosphere.

(6) The chemical sensor according to any one of Items (1) to (5),
in which the surface treatment is performed for areas of the on-chip lens, which are opposed to each other.

(7) The chemical sensor according to any one of Items (1) to (6),
in which the on-chip lens is provided to each of the photodiodes on a one-to-one basis and collects incident light to each of the photodiodes.

(8) The chemical sensor according to any one of Items (1) to (7), further including
a light shielding wall provided between the on-chip lenses.

(9) The chemical sensor according to any one of Items (1) to (8),
in which the flattening layer is made of a material having a refractive index difference with the on-chip lens of 0.4 or more.

(10) The chemical sensor according to any one of Items (1) to (9), further including
a probe material layer made of a probe material laminated on the flattening layer.

(11) The chemical sensor according to any one of Items (1) to (10),
in which a distance between the probe material layer and the photodiodes is 10 µm or less.

(12) The chemical sensor according to any one of Items (1) to (11),
in which the probe material layer is sectioned to face the on-chip lenses, respectively.

(13) The chemical sensor according to any one of Items (1) to (12),
in which the probe material is one of DNA, RNA, a protein, and an antigen.

(14) A chemical sensor module, including:
a chemical sensor including a substrate on which a plurality of photodiodes are formed to be arranged in a planar form, an on-chip lens to collect incident light to the photodiodes, which is provided on the substrate, and a flattening layer to cover and flatten the on-chip lens to form a probe holding surface for holding a probe material; and
an excitation light source to irradiate the chemical sensor with excitation light, the excitation light source being provided integrally to the chemical sensor.

(15) A biomolecule detection apparatus, including:
a chemical sensor including a substrate on which a plurality of photodiodes are formed to be arranged in a planar form, an on-chip lens to collect incident light to the photodiodes, which is provided on the substrate, and a flattening layer to cover and flatten the on-chip lens to form a probe holding surface for holding a probe material; and
a signal processing circuit to process an output signal of the photodiodes, which is connected to the chemical sensor.

(16) A biomolecule detection method, including:
preparing a chemical sensor including a substrate on which a plurality of photodiodes are formed to be arranged in a planar form, an on-chip lens to collect incident light to the photodiodes, which is provided on the substrate, and a flattening layer to cover and flatten the on-chip lens to form a probe holding surface for holding a probe material;
forming a probe material layer by laminating a probe material on the flattening layer;
bringing a measurement target substance into contact with the probe material layer to bond a target material contained in the measurement target substance with the probe material;
removing a measurement target substance which is not bonded with the probe material;
irradiating the chemical sensor with excitation light; and
detecting fluorescence caused by the bonding of the target material with the probe material by the photodiodes.

(17) The biomolecule detection method according to Item (16),
in which in the step of detecting the fluorescence, changes in wavelength and brightness of fluorescence by a mutual action of the target material and the probe material fluorescently labeled in advance are detected by the photodiodes.

(18) The biomolecule detection method according to Item (16) or (17),
in which in the step of detecting the fluorescence, fluorescence by a target material fluorescently labeled in advance and bonded with the probe material is detected by the photodiodes.

(19) The biomolecule detection method according to any one of Items (16) to (18),
in which in the step of detecting the fluorescence, a bonded body of the probe material and the target material is fluorescently labeled, and fluorescence thereof is detected by the photodiodes.

DESCRIPTION OF SYMBOLS 1 biomolecule detection apparatus
2 substrate
3 chemical sensor
21 photodiode
31 protection insulating layer
32 spectral layer
33 on-chip lens
34 antireflection layer
35 flattening layer
35a probe holding surface
36 surface layer
37 probe material layer
100 chemical sensor module
101 excitation light source
200 chemical sensor
201 light shielding wall

The invention claimed is:

1. A chemical sensor, comprising:
   a substrate;
   photodiodes at a surface of the substrate, each photodiode generating an electric charge in response to light incident thereon;
   on-chip lenses over the surface of the substrate and including at least one on-chip lens to collect respective incident light and direct the incident light to a respective photodiode, each on-chip lens having a convex shape that extends away from the substrate, each on-chip lens overlying a respective photodiode;
   a flattening layer covering the on-chip lenses and providing a flat surface over the on-chip lenses; and
   a probe material layer over the flattening layer flat surface.

2. The chemical sensor according to claim 1, wherein the incident light is fluorescence caused by bonding of probe material in the probe material layer with a target material.

3. The chemical sensor according to claim 1, further comprising a spectral layer made of a spectral material, the spectral layer laminated between the substrate and the on-chip lenses or between the on-chip lenses and the probe material layer.

4. The chemical sensor according to claim 1, further comprising a surface layer between flattening layer and the probe material layer.

5. The chemical sensor according to claim 4, wherein the surface layer is made of diamond and the at least one region is aminated.

6. The chemical sensor according to claim 5, wherein each region of the surface layer which overlies a photodiode is aminated.

7. The chemical sensor according to claim 1, further comprising light shielding walls between the on-chip lenses.

8. The chemical sensor according to claim 1, wherein the flattening layer is made of a material having a refractive index difference with the on-chip lens layer of 0.4 or more.

9. The chemical sensor according to claim 1, wherein the probe material layer is in direct contact with the flat surface of the flattening layer.

10. The chemical sensor according to claim 9, wherein a distance between the probe material layer and the at least one photodiode is 10 µm or less.

11. The chemical sensor according to claim 9, wherein the probe material layer is sectioned with each section overlying a respective on-chip lens.

12. The chemical sensor according to claim 1, wherein the probe material is DNA, RNA, a protein, or an antigen.

13. A biomolecule detection apparatus, comprising:
    a chemical sensor according to claim 1; and
    a signal processing circuit connected to the chemical sensor to process an output signal of each photodiode.

14. A chemical sensor module, comprising:
    a chemical sensor according to claim 1; and
    an excitation light source to irradiate the chemical sensor with excitation light, the excitation light source being provided integrally to the chemical sensor.

15. A sensor device comprising:
    a substrate having an upper surface;
    a plurality of photodiodes positioned at the upper surface;
    on-chip lenses over the photodiodes;
    a spectral layer between the on-chip lenses and the substrate;
    a surface layer;
    a probe material layer on the surface layer; and
    a flattening layer between the on-chip lenses and the surface layer,
    wherein,
       the surface layer has a plurality of regions, each region overlying a respective photodiode and each region effective to bond a respective section of the probe material layer thereto,
       each photodiode generates an electrical signal in response to respective incident light,
       each on-chip lens overlies a respective photodiode, and
       each on-chip lens has a convex shape the extends away from the substrate, and
       the flattening layer flattens the convex shapes and provides a flat surface on which the surface layer is positioned.

16. The sensor device of claim 15, wherein the flattening layer is made of a material having a refractive index difference with the on-chip lens layer of 0.4 or more.

17. The sensor device of claim 15, further comprising a light shielding walls between the on-chip lenses.

18. The sensor device of claim 15, further comprising an antireflection layer on the on-chip lenses.

19. The sensor device of claim 15, wherein the surface layer is made of diamond and each region is aminated.

* * * * *